(12) United States Patent
Ackerman et al.

(10) Patent No.: US 6,664,432 B2
(45) Date of Patent: Dec. 16, 2003

(54) HEAT TRANSFER IN THE ACID CATALYZED—EFFLUENT REFRIGERATED ALKYLATION PROCESS

(75) Inventors: Steven Ackerman, Fairfax, VA (US); Ian M. Fischer, Houston, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/409,321

(22) Filed: Apr. 8, 2003

(65) Prior Publication Data

US 2003/0216604 A1 Nov. 20, 2003

Related U.S. Application Data

(60) Provisional application No. 60/380,349, filed on May 14, 2002.

(51) Int. Cl.[7] .............................. C07C 2/56; C07C 2/58
(52) U.S. Cl. ........................ 585/715; 585/720; 585/911
(58) Field of Search ................................ 585/715, 720, 585/911

(56) References Cited

U.S. PATENT DOCUMENTS 2,416,760 A * 3/1947 Lawler et al. .............. 422/197

* cited by examiner

*Primary Examiner*—Thuan D. Dang
(74) *Attorney, Agent, or Firm*—Paul E. Purwin

(57) ABSTRACT

The acid catalyzed—effluent refrigerated alkylation of hydrocarbons in a shell and bare tube type alkylation reactor is improved by providing the bare tubes with internal inserts capable of increasing turbulence and mixing of refrigerant within the tubes whereby heat transfer in the process is enhanced.

11 Claims, 2 Drawing Sheets

HEAT TRANSFER IN THE ACID CATALYZED— EFFLUENT REFRIGERATED ALKYLATION PROCESS

A 35 U.S.C. 119(e) This application claims the benefit of U.S. Provisional Application(s) No(s).: APPLICATION NO(S).: 60/380,349 filed on May 14, 2002.

FIELD OF INVENTION

This invention relates generally to the alkylation of hydrocarbons in a shell and bare tube type alkylation reactor. More specifically the invention relates to enhancing the hydrocarbon alkylation process by improving the inside film heat transfer coefficient of bare tube type reactors.

BACKGROUND OF THE INVENTION

The process of alkylating isoparaffins with olefins in the presence of an acid catalyst to produce branched hydrocarbons, known as alkylates, is a well known commercially practiced process. Indeed there are four different commercial methods for carrying out this process. These are: sulfuric acid—autorefrigeration, sulfuric acid—effluent refrigeration, hydrofluoric acid-time tank, and hydrofluoric acid tubular reactor. In the case of sulfuric acid—effluent refrigeration, with which the present invention is concerned, a hydrocarbon effluent is flashed within a heat exchanger to cool the reaction zone. The reactor employed in this process is similar to a large shell-and-tube heat exchanger which is provided with a mixing impeller at the reactant inlet end of the reactor. The exothermic alkylation reaction occurs on the shell side of the reactor while flashing hydrocarbons within the tube provides the requisite cooling. The reactor operating temperature is determined mainly by olefin feed rate, isoparaffin concentration, feed stream inlet temperatures, mixing power, heat transfer area, heat transfer coefficient, and compressor suction pressure. Notwithstanding the foregoing the fixed amount of heat transfer surface area, i.e., the surface area of the bare tubes used in the reactor, is a significant factor contributing to the reactor operating at a temperature that is higher than what might be considered optimum.

In the alkyation reaction the lower the reactor temperature the lower the acid consumption, the greater the yield of alkylate and the better the quality of alkylate. One way the reaction temperature can be lowered is by increasing refrigeration compressor capacity (e.g., lower suction pressure); however, this is costly and therefore other techniques to enhance heat removal to maintain a more desirable reaction temperature condition have been proposed. For example, the use:o enhanced nucleate boiling surfaces to increase the heat transfer film coefficient on the boiling side heat transfer surface is disclosed in U.S. Pat. No. 4,769,511.

As is pointed out in U.S. Pat. No. 5,625,112 use of enhanced boiling surfaces in the operation of some heat exchangers does not always provide a benefit. Indeed U.S. Pat. No. 5,811,625 teaches that enhanced boiling surfaces in an acid catalyzed alkylation process provided little or no benefit. In other words heat transfer tubes coated with an enhanced surface on their inside perform at essentially the same heat transfer rates as bare tubes.

SUMMARY OF INVENTION

Now it has been discovered, that bare heat transfer tubes fitted internally with inserts capable of increasing turbulence and mixing within the tube result in enhanced heat transfer in the acid catalyzed—effluent refrigerated alkylation process.

In one embodiment, this invention is a process for a alkylating isoparaffinic hydrocarbons with olefinic hydrocarbons in the presence of an acid catalyst. The process includes steps of reacting the isoparaffinic hydrocarbons and olefinic hydrocarbons in the presence of acid catalyst to form alkylate, separating a hydrocarbon mixture into an acid phase and a hydrocarbon phase, reducing the pressure on the hydrocarbon phase to refrigerate and vaporize volatile hydrocarbons and passing the refrigerated hydrocarbon phase through the interior of a plurality of heat exchange tubes. Vaporization of the hydro-carbons in contact with the interior surface effects indirect heat exchange to cool the reaction mixture which is in contact with the exterior of the heat exchange tubes. This invention improves the alkylation process by passing the hydro-carbon phase to heat exchange tubes fitted with inserts capable of increasing turbulence and mixing within the tube whereby heat transfer coefficient is increased.

Additional objects, embodiments, and details of this invention are set forth in the following detailed description of the invention.

DETAILED DESCRIPTION OF THE INVENTION

Figure 1:
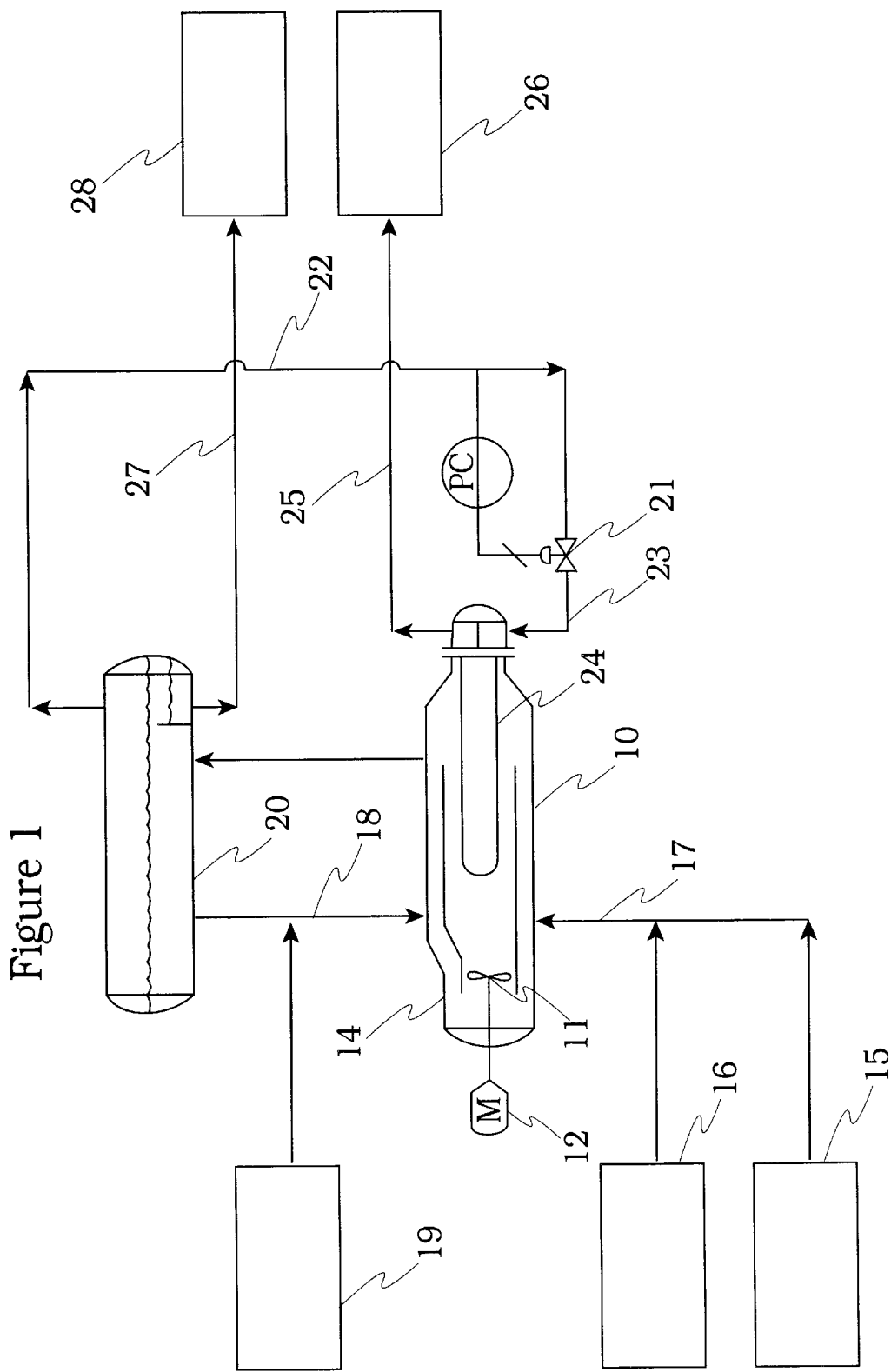
FIG. 1 is a simplified flow diagram of an alkylation process reactor system.

A simplified drawing of a sulfuric acid-effluent refrigerated alkylation process reactor system including a shell-and-tube type reactor is shown in FIG. 1. As shown the reactor 10 is configured similar to a large shell-and-tube heat exchanger. A single mixing impeller 11 is located at the reactant inlet end 14 of reactor 10. The mixing impeller 11 is operably connected to drive means such as turbine or motor 12. The reaction, of course, takes place on the shell side of the reactor. Premixed olefin feed plus recycled isoparaffin, such as isobutane from supply source 15, and recycled refrigerant from supply source 16 are injected into the eye of the mixing impeller 11 via line 17. Also injected into the eye of the mixing impeller 11 via line 18 is acid catalyst from acid supply source 19 and acid settler 20. Shell side operating pressure is kept sufficiently high to avoid vaporization. Thus, a pressure in the range of about 50 to 100 psig is maintained therein. Hydrocarbons from the settler 20 are sent via line 22, flashed across a control valve 21 and fed via line 23 to the tube side 24 of reactor 10. The vaporization of hydrocarbons in the tubes 24 provides further cooling of the reactor 10. The hydrocarbons are then routed via line 25 to knock out drum 26 where vapors are sent to a refrigeration compressor (not shown). Spent acid is sent via line 27 to tankage 28 (not shown) and eventual regeneration. Liquid from knock out drum 26 proceeds to the treating and fractionation section (not shown) of the alkylation plant for recycle of isoparaffin and recovery of alkylate product.

A key feature of the present invention is providing the side heat transfer tube with inserts capable of increasing turbulence and mixing the hydrocarbons within the tube.

By increasing turbulence and mixing within the reactor tubes the inserts, in effect, increases the liquid contact with the surface thereby increasing the inside heat transfer coefficient. The increased turbulence, however, also increases the pressure drop in the tube side over that when no tube insert is used. The added pressure drop increases the boiling temperature of the refrigerant in the tubes which reduces the driving temperature difference for heat transfer. If the pressure drop is high enough, the benefits of improved heat transfer can be negated by loss of temperature driving force. Consequently, the tube inserts are designed to provide a relative pressure drop increase over a bare tube pressure drop of not more than about 3 times and preferably not more than about 1.5 to 2.0 times.

Figure 2:
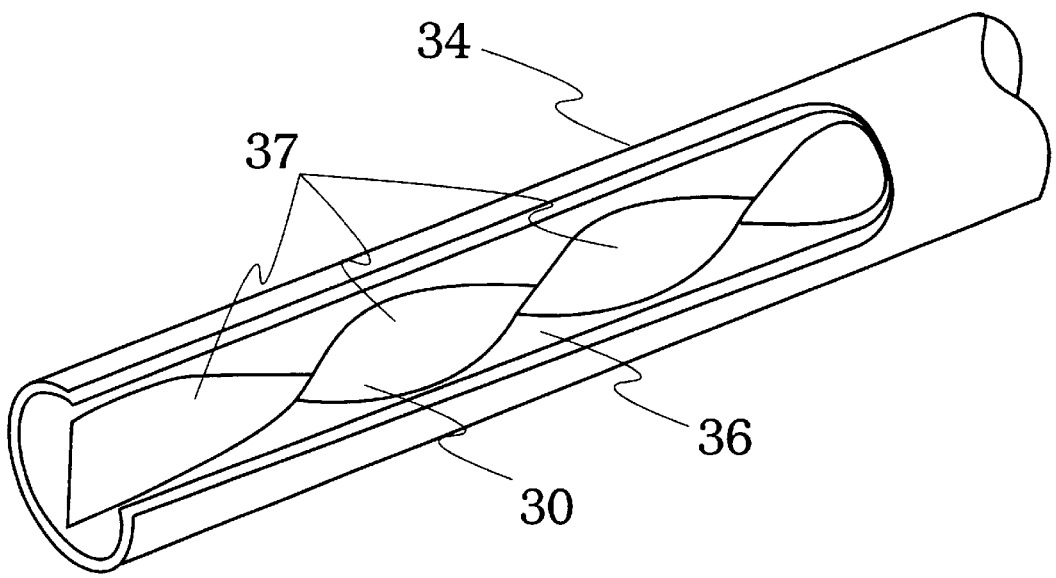
FIG. 2 is simplified drawing illustrating a tube insert suitable in the practice of the invention.

One particularly useful tube insert is shown in FIG. 2. As shown tube insert 30 is in the form of a twisted strip or tape sized to fit easily within tube 34. Thus the width of the tape will be slightly less than the diameter of tube 34 to permit it to be easily positioned within tube 34. The overall length of tube insert 30 will be substantially the same as the straight run portion of tubes 24 shown in FIG. 1. As is shown in FIG. 2 the insert 30 has a plurality of segment 37 of substantially the same length but of different pitch.

An advantage of the present invention is, of course, the ability to retrofit bare tube alkylation reactors at relatively modest cost.

EXAMPLE

A comparison is made between operating an alkylation process with 8 reactors all having bare tubes some or all of the reactors having tube inserts in accordance with the invention. The reactor operating conditions are given in Table 1. The details of the comparisons are given in Table 2.

TABLE 1

| Operating Conditions of Alkylation Process | |
|---|---|
| Acid-in-emulsion, LV % | 50 |
| Olefin Space Velocity, v/hr/v (weighted average) | 0.270 |
| Reactor Temperature, ° F. (weighted average) | 46.0 |
| Fresh acid strength, wt % | 98.5 |
| Spent Acid Strength, wt % | 91.4 |
| Isobutane in reactor product, LV % | 57.5 |
| Trap drum pressure, psig | 2.0 |
| Reactor effluent, kBSD | 62.6 |
| DIB feed, kBSD | 26.6 |
| Recycle Refrigerant, kBSD | 34.9 |

TABLE 2

Example of Improved Alkylation Process With Enhanced Reactor Heat Transfer

AVERAGE ALKYLATE PRODUCTION

| Case | Base | 1 | 2 | 3 | 4 |
|---|---|---|---|---|---|
| Enhanced Tube Bundle (1) | | | | | |
| R-1001/R-1002 R-1/R-2 | No | No | No | No | Yes |
| R-1003/R-1004 R-3/R-4 | No | No | No | Yes | Yes |
| R-1005/R-1006 R-5/R-6 | No | No | Yes | Yes | Yes |
| R-1007/R-1008 R-7/R-8 | No | Yes | Yes | Yes | Yes |
| Total Surface Area ft2 | 68000 | 68000 | 68000 | 68000 | 68000 |
| Relative Overall U A, Btu/hr-F | 1.000 | 1.070 | 1.140 | 1.210 | 1.280 |
| Reactor Temperature F (2) | | | | | |
| R-1001/R-1002 R-1/R-2 | 46.4 | 46.4 | 46.4 | 46.4 | 44.9 |
| R-1003/R-1004 R-3/R-4 | 46.0 | 46.0 | 46.0 | 44.5 | 44.5 |
| R-1005/R-1006 R-5/R-6 | 45.9 | 45.9 | 44.4 | 44.4 | 44.4 |
| R-1007/R-1008 R-7/R-8 | 45.7 | 44.3 | 44.3 | 44.3 | 44.3 |
| Average | 46.0 | 45.7 | 45.3 | 44.9 | 44.5 |
| Delta | Base | −0.3 | −0.7 | −1.1 | −1.5 |
| Yields | | | | | |
| C5 + alkylate, BPSD | 11877 | 11878 | 11881 | 11884 | 11887 |
| Delta C5 +, BPSD | Base | 1 | 4 | 7 | 10 |
| iC4 consumed, BPSD | 7914 | 7915 | 7917 | 7919 | 7922 |
| Delta iC4, BPSD | Base | 1 | 3 | 5 | 8 |
| Alkylate Octane | | | | | |
| C5 + RONc | 93.37 | 93.38. | 93.40 | 93.43 | 93.47 |
| C5 + MONc | 91.84 | 91.85 | 91.86 | 91.88 | 91.90 |
| C5 + OI | 92.61 | 92.62 | 92.63 | 92.66 | 92.69 |
| Delta OIB/day | Base | 122 | 311 | 619 | 987 |
| Fresh Acid | | | | | |
| Rate, BPSD | 415 | 409 | 403 | 398 | 392 |
| Delta, BPSD | Base | −6 | 12 | −17 | −23 |

(1) Bare tube bundles are not replaced, but inserts are added resulting in 28% increase in overall heat transfer coefficient. Tubeside pressure drop increases by 1.7 factor.
(2) Reactor temperature for enhanced tube cases reflect 70% increase in tubeside pressure drop over the base case.

What is claimed is:

1. In the acid catalyzed—effluent refrigerated alkylation process wherein a refrigerant is passed through bare tube in an alkylation reactor the improvement comprising providing the tubes with internal inserts capable of increasing turbulence and mixing of refrigerant within the tubes whereby the heat transfer of the refrigerant is enhanced.

2. The improvement of claim 1 wherein the inserts increase the pressure drop in the tube relative to bare tubes less than about 3 times.

3. The improvement of claim 2 wherein the inserts increase the pressure drop not more than about 1.5 to 2.0 times.

4. The improvement of claim 2 or 3 wherein the insert is in the form of a twisted tape.

5. The improvement of claim 4 wherein the insert has a width such that the insert can be easily positioned within the bare tubes.

6. The improvement of claim 5 wherein the insert has a plurality of segments of substantially the same length and of different pitch.

7. The improvement of claim 6 wherein the tubes in the alkylation reactor have a straight run portion and a curved portion and the inserts have a length substantially the same as the straight run portion of the tubes.

8. In a process of alkylating is oparaffinic hydrocarbon with olefinic hydrocarbons in the presence of an acid catalyst in a reaction zone to form alkylate wherein a mixture of hydrocarbons with acid catalyst is withdrawn as effluent from the reaction zone and separated into an acid phase and a hydro-carbon phase and which separated hydrocarbon phase is refrigerated and passed through tubes located in the reaction zone for indirect heat exchange with the hydrocarbons and catalyst, the improvement comprising providing the tubes with internal inserts capable of increasing turbulence within the tube whereby the heat transfer coefficient is enhanced.

9. The improvement of claim 8 wherein the inserts increase the pressure drop in the tubes relative to bare tubes of less than about 3 times.

10. The improvement of claim 9 wherein the inserts are in the form of a twisted tape.

11. The improvement of claim 10 wherein the inserts increase the pressure drop in the tubes not more than about 1.5 to 2.0 times that of the bare tubes.

* * * * *